US012672921B2

(12) United States Patent (10) Patent No.: US 12,672,921 B2
Govari et al. (45) Date of Patent: Jul. 7, 2026

(54) MONITORING TORSION ON A DISTAL END ASSEMBLY

(71) Applicant: BIOSENSE WEBSTER (ISRAEL) LTD., Yokneam (IL)

(72) Inventors: Assaf Govari, Haifa (IL); Vadim Gliner, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 253 days.

(21) Appl. No.: 18/530,487

(22) Filed: Dec. 6, 2023

(65) Prior Publication Data

US 2025/0186125 A1 Jun. 12, 2025

(51) Int. Cl.
*A61B 34/20* (2016.01)
*A61B 18/00* (2006.01)
(Continued)

(52) U.S. Cl.
CPC .......... *A61B 34/20* (2016.02); *A61B 18/1492* (2013.01); *A61B 2018/0022* (2013.01); *A61B 2018/00267* (2013.01); *A61B 2018/00375* (2013.01); *A61B 2018/00577* (2013.01); *A61B 2034/2051* (2016.02); *A61B 2090/066* (2016.02)

(58) Field of Classification Search
CPC ................ A61B 34/20; A61B 18/1492; A61B 2034/2051; A61B 2090/066; A61B 2018/0022; A61B 2018/00267; A61B 2018/00375; A61B 2018/00577
See application file for complete search history.

(56) References Cited

U.S. PATENT DOCUMENTS 5,391,199 A 2/1995 Ben Haim
5,443,489 A 8/1995 Ben Haim
(Continued)

FOREIGN PATENT DOCUMENTS

EP 2196143 B1 * 8/2012 ......... A61B 18/1492

OTHER PUBLICATIONS

Soltani, "A Three-Dimensional Shape-Based Force and Stiffness-Sensing Platform for Tendon-Driven Catheters", Jun. 28, 2016, MDPI (Year: 2016).*
(Continued)

*Primary Examiner* — Linda C Dvorak
*Assistant Examiner* — Abigail Bock
(74) *Attorney, Agent, or Firm* — FBT Gibbons LLP

(57) ABSTRACT

Apparatus for measuring a torque, consisting of a probe having a shaft with a shaft distal end. The probe has a distal end assembly, configured to be inserted into an organ of a human subject, and having a distal termination and a proximal termination connected to the shaft distal end. A position sensor assembly is attached to the distal end assembly in proximity to the distal termination, the position sensor assembly being configured to provide signals indicative of a three-dimensional position and orientation of the distal termination with respect to the shaft distal end. A processor is configured to compute a torsion of the distal termination with respect to the proximal termination in response to the signals from the position sensor assembly, and compute the torque on the distal end assembly in response to the torsion and a predetermined correspondence between the torsion and the torque.

20 Claims, 5 Drawing Sheets

(51) Int. Cl.
　　　*A61B 18/14*　　　(2006.01)
　　　*A61B 90/00*　　　(2016.01)

(56)　　　　　　　References Cited

U.S. PATENT DOCUMENTS

| | | | | |
|---|---|---|---|---|
| 5,558,091 | A | 9/1996 | Acker | |
| 6,172,499 | B1 | 1/2001 | Ashe | |
| 6,239,724 | B1 | 5/2001 | Doron | |
| 6,332,089 | B1 | 12/2001 | Acker | |
| 6,484,118 | B1 | 11/2002 | Govari | |
| 6,618,612 | B1 | 9/2003 | Acker | |
| 6,690,963 | B2 | 2/2004 | Ben Haim | |
| 6,788,967 | B2 | 9/2004 | Ben Haim | |
| 6,892,091 | B1 | 5/2005 | Ben Haim | |
| 11,596,324 | B2 | 3/2023 | Gliner | |
| 2013/0131489 | A1* | 5/2013 | Altmann | A61B 5/05 |
| | | | | 606/41 |
| 2020/0206461 | A1* | 7/2020 | Govari | A61B 5/066 |
| 2021/0077180 | A1* | 3/2021 | Beeckler | A61B 18/1492 |
| 2021/0330213 | A1 | 10/2021 | Papini | |
| 2022/0387101 | A1* | 12/2022 | Olson | A61M 25/01 |

OTHER PUBLICATIONS

Extended European Search Report, received for European Application No. 24217628.7, mailed on May 7, 2025, 10 pages.

\* cited by examiner

300

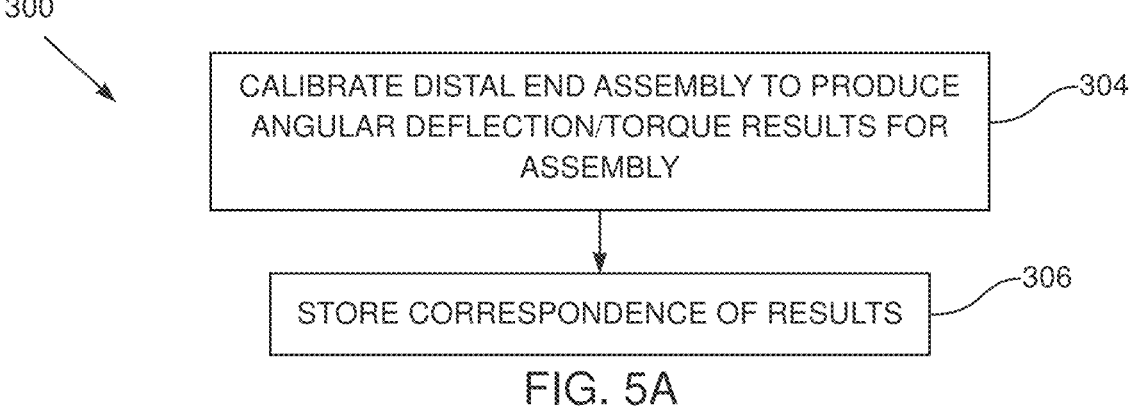

CALIBRATE DISTAL END ASSEMBLY TO PRODUCE ANGULAR DEFLECTION/TORQUE RESULTS FOR ASSEMBLY ——304

STORE CORRESPONDENCE OF RESULTS ——306

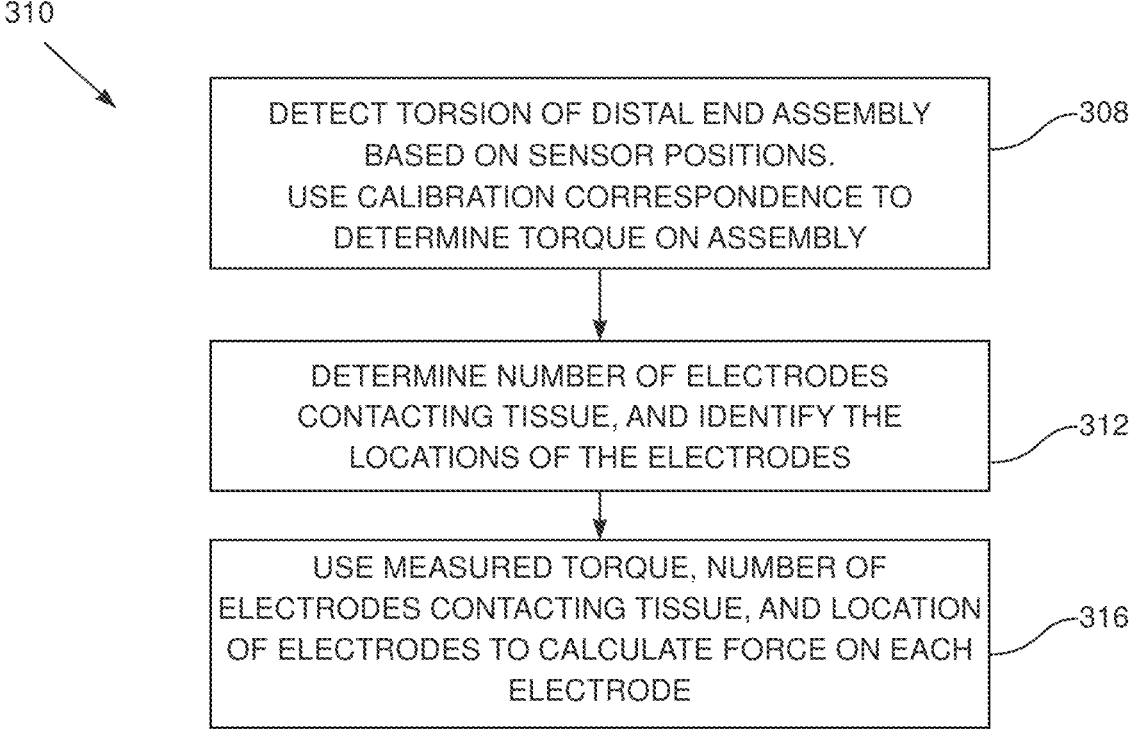

DETECT TORSION OF DISTAL END ASSEMBLY BASED ON SENSOR POSITIONS. USE CALIBRATION CORRESPONDENCE TO DETERMINE TORQUE ON ASSEMBLY ——308

DETERMINE NUMBER OF ELECTRODES CONTACTING TISSUE, AND IDENTIFY THE LOCATIONS OF THE ELECTRODES ——312

USE MEASURED TORQUE, NUMBER OF ELECTRODES CONTACTING TISSUE, AND LOCATION OF ELECTRODES TO CALCULATE FORCE ON EACH ELECTRODE ——316

FIG. 5B

MONITORING TORSION ON A DISTAL END ASSEMBLY

FIELD OF THE DISCLOSURE

This disclosure relates generally to catheters and specifically to measuring force on the catheters.

BACKGROUND

In a catheter configured to ablate tissue, a distal end assembly of the catheter may be maneuvered to a target region of the tissue. Electrodes on the distal end assembly may then be used to ablate to the target region tissue.

BRIEF DESCRIPTION OF THE DRAWINGS

The present disclosure will be understood from the following detailed description, taken in conjunction with the drawings in which:

FIG. 5A is a flowchart describing a calibration algorithm performed by a processor of the system, according to an example of the present disclosure; and FIG. 5B is a flowchart describing an operational algorithm performed by the processor during an ablation procedure, according to an example of the present disclosure.

DESCRIPTION OF EXAMPLES

Overview

Catheters having a distal end assembly that is in the form of a basket or a balloon may be advantageously used for ablation, for example in the ostium of a pulmonary vein. Once the distal end assembly has been correctly positioned, a circular ablation line may be generated by simultaneously energizing multiple electrodes of the assembly. The simultaneity reduces the overall time of the ablation procedure.

In the case of a basket distal end assembly splines of the assembly are flexible, so that the assembly may be maneuvered into a desired location in the heart, and so that the electrodes on the splines better conform to the shape of the tissue being ablated. However, the flexibility of the splines means that as the distal end assembly is maneuvered into position, the assembly as a whole may twist relative to the shaft of the catheter, when the electrodes are in contact with the tissue. Also in the case of a balloon the assembly may twist relative to the shaft. In addition to twisting, the distal end assembly may be pressed against the tissue.

A torque may be established between the twisted distal end assembly and the tissue that is contacted while the physician is manipulating and/or positioning the catheter at a selected ablation site. The quality and extent of an ablation performed by an electrode is dependent on the force applied by the electrode to the tissue. It is important to account for the torque when accessing the force applied on the individual electrodes.

An example of the present disclosure provides a method for determining the torque produced by the distal end assembly, by sensing the torsion, i.e., the angular rotation, of the distal tip of the assembly relative to shaft. A plurality of position sensors are attached close to the distal tip of the distal end assembly. During a procedure, e.g., an ablation procedure locations and orientations of the sensors with respect to the shaft are measured, and from the measurements the torsion of the distal tip, about an axis defined by the shaft of the catheter, is calculated.

A calibration procedure, performed prior to the ablation procedure finds a correspondence between the angular rotation, i.e., the torsion, produced and the torque generating the rotation. In one example the correspondence is model-based and assumes that the distal end assembly behaves elastically. The correspondence is then used in the ablation procedure to find the overall torque on the assembly from the measured angular rotation. During the ablation procedure electrodes of the distal assembly that are in contact with tissue are identified. Since the positions of the contacting electrodes of the distal end assembly are known, the force on each of the electrodes may be calculated from the overall torque.

System Description

In the following description, like elements are identified by the same numeral, and are differentiated, where required, by having a letter attached as a suffix to the numeral.

Figure 1:
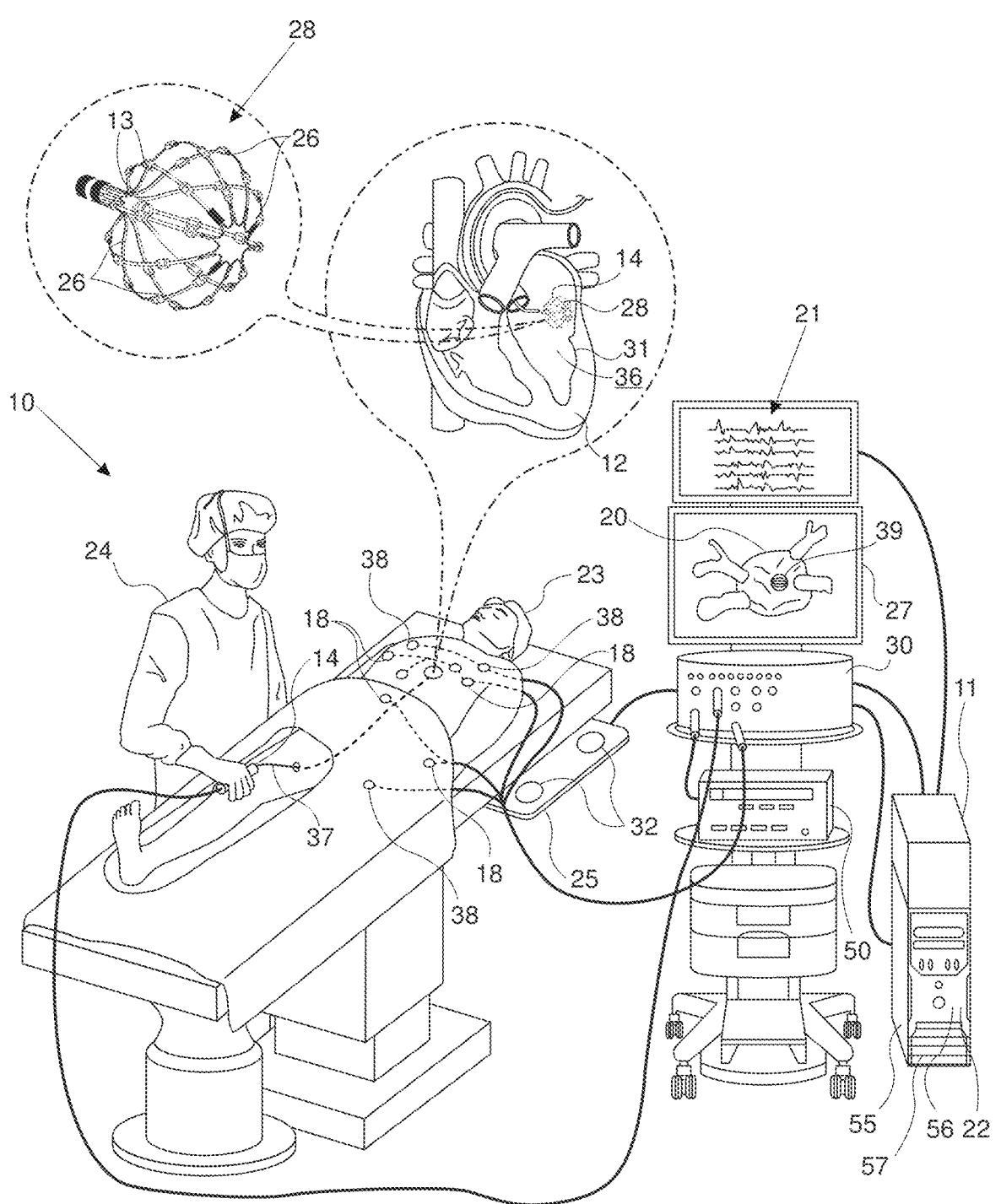
FIG. 1 shows a catheter-based electrophysiology mapping and ablation system being used for a medical procedure, according to an example of the present disclosure.

Reference is now made to FIG. 1 which shows a catheter-based electrophysiology mapping and ablation system 10 being used for a medical procedure, according to an example of the present disclosure. System 10 includes multiple catheters, which are percutaneously inserted by a physician 24 through the patient's vascular system into a chamber or vascular structure of a heart 12 of a patient 23. Typically, a delivery sheath catheter is inserted into the left or right atrium near a desired location in heart 12. Thereafter, a plurality of catheters can be inserted into the delivery sheath catheter so as to arrive at the desired location. The plurality of catheters may include catheters dedicated for sensing Intracardiac Electrogram (IEGM) signals, catheters dedicated for ablating, and/or catheters dedicated for both sensing and ablating.

An example catheter 14, also referred to herein as probe 14, that is configured for an ablation procedure is illustrated herein, the probe comprising an insertion shaft 37 and a distal end assembly 28 fixed to a distal end of the shaft. During the ablation procedure, once distal end assembly 28 exits the delivery sheath, physician 24 manipulates a proximal end of shaft 37, so as to bring the assembly into contact with a heart wall 31 of a chamber 36 of heart 12, for the purpose of ablating a target site in the wall.

Figure 2A:
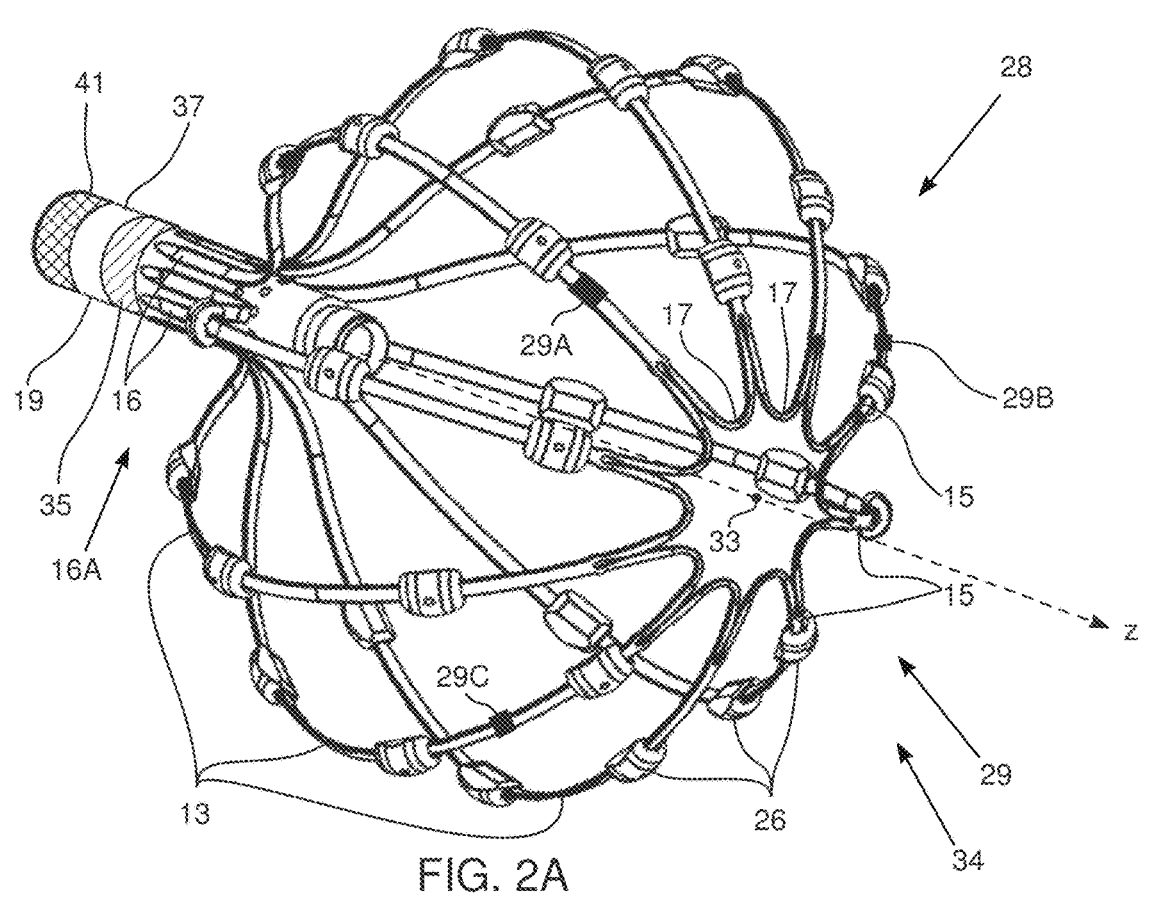
FIG. 2A is a schematic diagram of a distal end assembly, in an unconstrained form, used in the system, according to an example of the present invention.
Figure 2B:
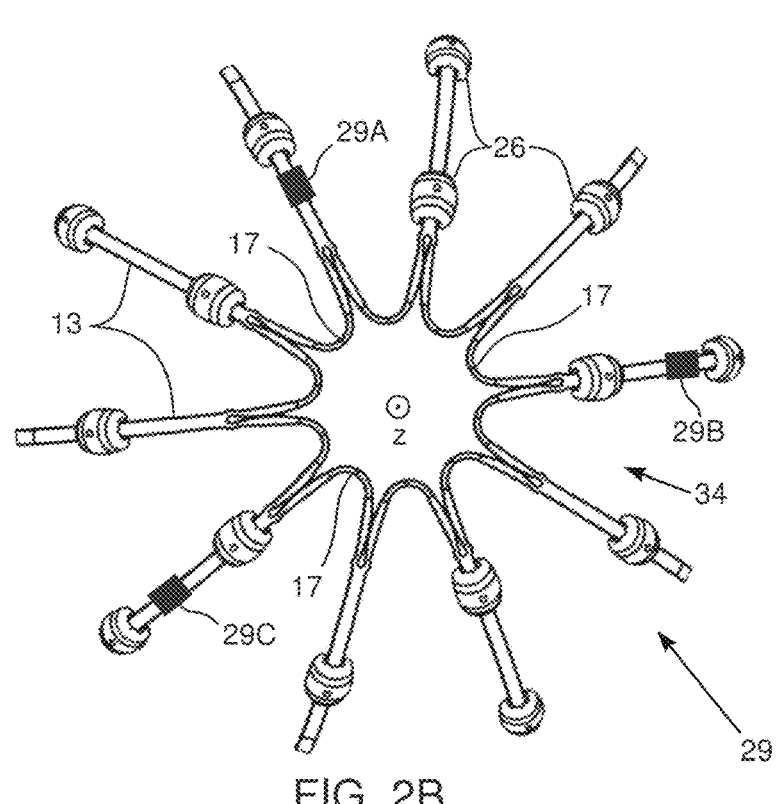
FIG. 2B is a schematic view of the unconstrained assembly along an assembly axis, according to an example of the present invention.

FIG. 2A is a schematic diagram of distal end assembly 28 in a fully deployed unconstrained form, i.e., with no contact force applied on the distal end assembly, and FIG. 2B is a schematic view of the unconstrained assembly along an assembly axis, according to an example of the present invention. In the description herein, except where otherwise stated, catheter 14 is assumed to comprise a basket catheter, so that distal end assembly 28 is a basket that is constructed as a plurality of similar resilient splines 13A, 13B, . . . , generically termed splines 13. Splines 13 form assembly 28 to have a generally spheroidal shape and act as a supporting structure for attached electrodes 26, so may also herein be termed supporting structure 13. Each of the splines of structure 13 has at least one attached electrode 26 which may be used for ablation. Each spline has a known length, and each attached electrode 26 is in a known location on its respective spline. Respective proximal terminations 16 of the splines are fixedly located at a distal end 19 of shaft 37, and together act as a proximal termination of distal end assembly 28. Distal terminations 15 of the splines bifurcate, the bifurcations are connected together by substantially rigid loops 17 joining adjacent splines. Other structures for connecting distal terminations 15 are contemplated herein. A distal structure 34 of the assembly, herein, by way of example, optionally including loops 17, formed by connection of distal terminations 15 is typically substantially rigid. Distal structure 34 acts as a distal termination of distal end assembly 28.

In the example of distal end assembly 28 illustrated in FIGS. 2A and 2B there are ten splines 13 distributed about an assembly axis, herein termed a z-axis, collinear with a central axis of symmetry of distal end 19 of shaft 37. However, it will be understood that assembly 28 may have more or less than ten distributed splines.

As is illustrated in FIG. 2A, terminations 15 of splines 13 are proximate to a distal point 33 that is centered on structure 34, and the z-axis comprises a line from the distal point to the center of shaft 37. Terminations 15 are distributed symmetrically about distal point 33.

A position sensor 35 is located at distal end 19 of shaft 37. In addition, a plurality of generally similar position sensors 29A, 29B, . . . are attached to respective different splines 13A, 13B, . . . in proximity to distal terminations 15 of the splines. Sensors 29A, 29B, . . . operate as a position sensor assembly 29, and are attached to their respective splines so that they are in a three-dimensional (3D) configuration. It will be understood that since the splines are angled with respect to each other, in the 3D configuration axes of their attached sensors are also angled with respect to each other. By having the sensors angled in this manner, even if the sensors are magnetic based single axis sensors, signals from the plurality of sensors provide full 3D information for the attached splines. In a disclosed example, as illustrated, there are three position sensors 29A, 29B, and 29C respectively on splines 13A, 13B, and 13C, but other examples may have more or fewer than three sensors.

The splines to which sensors of assembly 29 are attached are selected so that the sensors are distributed at least approximately symmetrically about the z-axis. Thus, in the disclosed example using splines 13A, 13B, and 13C, where the ten splines 13 are separated by 36°, the angles between splines 13A, 13B, and 13C, are 108°, 108°, and 144°. Selecting the splines to be approximately symmetrically distributed ensures that adjacent sensors of the splines are separated as much as possible.

Position sensor 35 and position sensors of assembly 29 are typically magnetic based position sensors having at least one coil. In a disclosed example, position sensor 35 is a two or a three axis coil, and sensors of assembly 29 are single axis coils. Sensors 35 and sensors of assembly 29 may be operated using a location pad 25 including a plurality of magnetic coils 32 configured to generate magnetic fields in a predefined working volume. The real time position of multi-axis sensor 35, i.e., the three-dimensional (3D) location and 3D orientation of the sensor, may be tracked based on magnetic fields generated with location pad 25 and sensed by the sensor. Similarly, the real time positions of single axis sensors of assembly 29, i.e., their 3D locations and 2D orientations, may be tracked based on the magnetic fields from location pad 25. Details of magnetic based position sensing technology are described in U.S. Pat. Nos. 5,5391,199; 5,443,489; 5,558,091; 6,172,499; 6,239,724; 6,332,089; 6,484,118; 6,618,612; 6,690,963; 6,788,967; 6,892,091.

In some examples one or more coils 41 are located at distal end 19, and the coils are configured to generate a magnetic field, in a generally similar manner to the coils of location pad 25. The magnetic field from coils 41 enables the positions of sensors of assembly 29 relative to coils 41 to be tracked. U.S. Patent Publication 2020/0206461 provides details of a magnetic tracking system similar to that using coils 41, wherein a magnetic field generator on a basket catheter shaft is used to find positions of sensors on the basket.

In some examples sensor 35 is configured to operate, either sequentially or simultaneously, as a position sensor and as a magnetic field generator. When operated in this mode, the position of sensor 35 relative to location pad 25 is determined using fields from the location pad, and the positions of sensors of assembly 29 are determined relative to coils 41 (from its magnetic fields) and also relative to location pad 25.

It will be appreciated that the unconstrained form of distal end assembly 28, illustrated in FIG. 2A, exists before the assembly enters the delivery sheath referred to above. As stated above, during an ablation procedure, physician 24 manipulates a proximal end of catheter shaft 37 to bring distal end assembly 28 into contact with heart wall 31. The manipulation typically involves physician 24 pushing, pulling, flexing, and/or turning the proximal end of shaft 37 to bring assembly 28 into a desired location contacting wall 31.

When at least some electrodes 26 of distal end assembly are in contact with wall 31, the assembly may be twisted from its unconstrained form with respect to shaft 37. In the constrained, twisted, form of the assembly tissue in contact with the electrodes exerts respective forces on the electrodes, producing a torque on the assembly, and the electrodes exert respective countervailing forces on the tissue. The description below, with regards to FIG. 5, describes how examples of the disclosure ascertain both the torque on the assembly and the forces on the assembly electrodes due to the torque.

Figure 3:
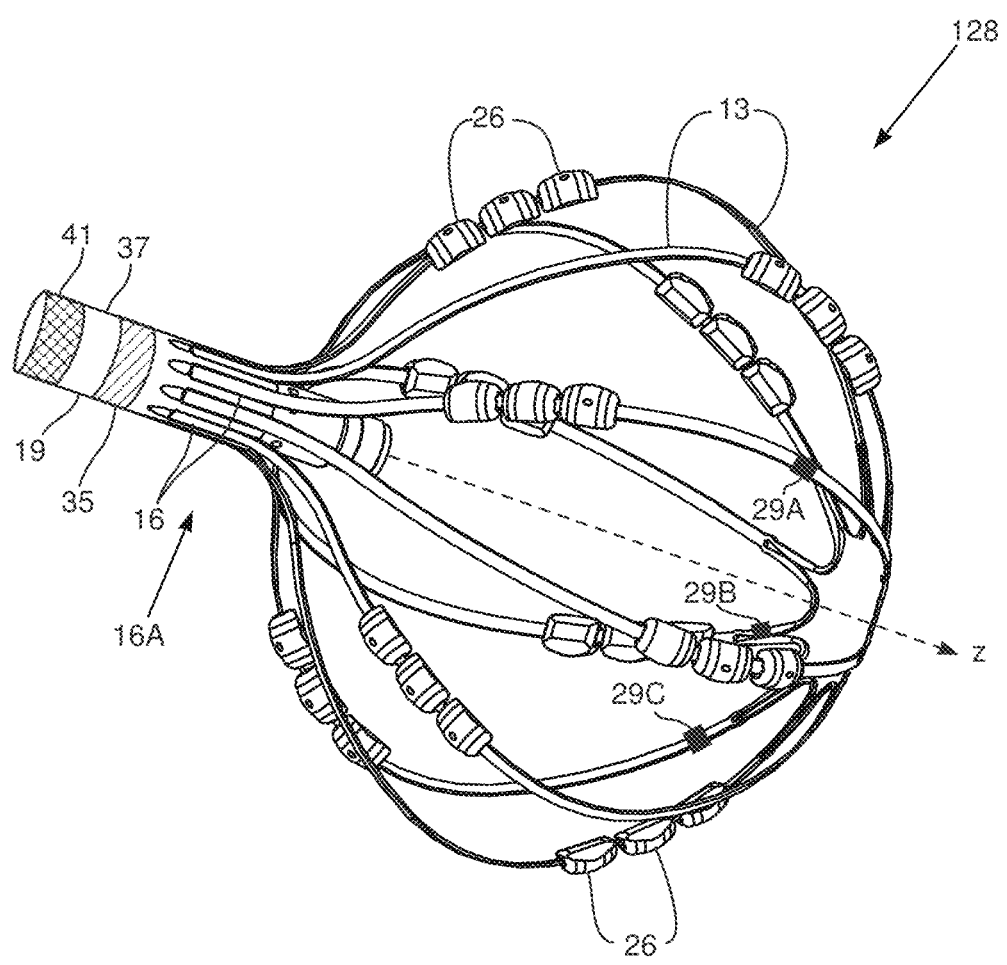
FIG. 3 is a schematic diagram of an alternative distal end assembly, according to an example of the present disclosure.

FIG. 3 is a schematic diagram of an alternative distal end assembly 128, according to an example of the present disclosure. Apart from the differences described below, the operation of assembly 128 is generally similar to that of assembly 28 (FIGS. 2A and 2B), and elements indicated by the same reference numerals in both assembly 28 and assembly 128 are generally similar in construction and in operation. In contrast to assembly 28, wherein electrodes 26 are attached as single electrodes, in assembly 128 electrodes 26 are attached in groups. By way of example, in the illustrated example of assembly 128 electrodes 26 are in groups of three. As for assembly 28, in assembly 128 sensors of assembly 29 are at a distal section of assembly 128 in a 3D configuration.

Figure 4:
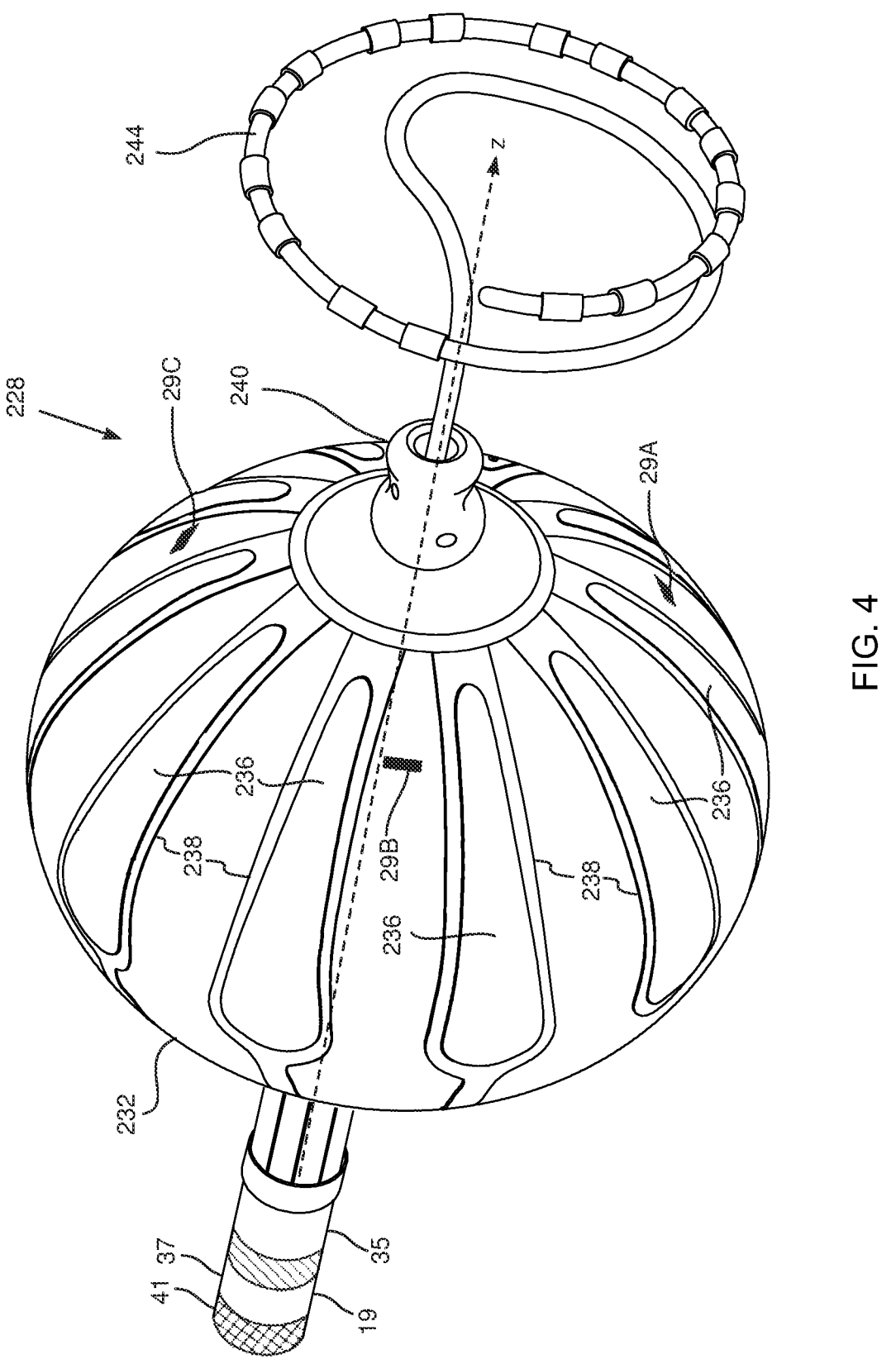
FIG. 4 is a schematic diagram of a further alternative distal end assembly, according to an example of the present disclosure.

FIG. 4 is a schematic diagram of a further alternative distal end assembly 228, according to an example of the present disclosure. Apart from the differences described below, the operation of assembly 228 is generally similar to that of assemblies 28 and 128 (FIGS. 2A, 2B and 3), and elements indicated by the same reference numerals in assemblies 28, 128 and 228 are generally similar in construction and in operation.

In contrast to assemblies 28 and 128, distal end assembly 228 is formed as a balloon assembly, having a balloon 232 which, when inflated, has a generally spheroidal as shape. Balloon 232 acts a supporting structure for ablation electrodes 236 attached, via electrode substrates 238, to the balloon, and so may herein also be termed supporting structure 232. In FIG. 4 assembly 228 is illustrated with balloon 232 in its inflated state attached to shaft 37.

A balloon termination 240 is at the distal end of the balloon and, together with the center of shaft 37 defines a z-axis as an axis for assembly 228. (A lasso catheter 244 is illustrated as extending from balloon termination 240, and may be used to position balloon assembly 228 in a desired location.) As for assemblies 28 and 128, position sensors of assembly 29 (in the example illustrated there are three sensors 29A, 29B, 29C) are attached to balloon 232 proximate to termination 240 in the 3D configuration described above.

For simplicity and clarity, the following description relates to distal end assembly 28, and those having ordinary skill in the art will be able to adapt the description, mutatis mutandis, for other distal end assemblies such as assembly 128 and assembly 228. Thus, the scope of the present disclosure includes other basket catheters having distal end assemblies comprising pluralities of resilient splines, each of the splines having at least one electrode useable for ablation. The scope of the present disclosure also includes other balloon catheters having balloons with attached electrodes suitable for ablation.

Returning to FIG. 1, system 10 includes one or more electrode patches 38 positioned for skin contact on patient 23. Measurements of the impedance between patches 38 and a given electrode 26 may be used to identify if the electrode is contacting tissue of wall 31. U.S. Pat. No. 11,596,324 describes how the impedance between an electrode on a basket catheter and patches on the skin of a patient may be used to identify if the electrode is contacting tissue in a chamber of an organ of the patient. Optionally, impedance between intracardiac electrodes may be sensed to assess contact with the cavity wall. The intracardiac electrodes may include electrodes on the distal end assembly and/or electrodes on a distal end of the catheter shaft.

A recorder 11 displays electrograms 21 captured with surface body ECG 18 electrodes and intracardiac electrograms (IEGM) that may be captured with electrodes 26 of catheter 14. Recorder 11 may include pacing capability for pacing the heart rhythm and/or may be electrically connected to a standalone pacer.

System 10 may include an ablation energy generator 50 that is adapted to conduct ablative energy to one or more of electrodes 26. Energy produced by ablation energy generator 50 may include, but is not limited to, radiofrequency (RF) energy or pulsed-field ablation (PFA) energy, including monopolar or bipolar high-voltage DC pulses as may to be used effect irreversible electroporation (IRE), or combinations thereof.

A patient interface unit (PIU) 30 is an interface configured to establish electrical communication between catheters, electrophysiological equipment, a power supply and a workstation 55 for controlling operation of system 10. Electrophysiological equipment of system 10 may include for example, multiple catheters, location pad 25, body surface ECG electrodes 18, electrode patches 38, ablation energy generator 50, and recorder 11. Optionally and preferably, PIU 30 additionally includes processing capability for implementing real-time computations of location of the catheters and for performing ECG calculations.

Workstation 55 includes memory, a processor 22 with memory or storage with appropriate operating software loaded therein, and user interface capability. Processor 22 operates system 10. Workstation 55 may provide multiple functions, optionally including (1) modeling the endocardial anatomy in three-dimensions (3D) and rendering a model or anatomical map 20 of heart 12 or a portion thereof for display on a display device 27, (2) displaying on display device 27 activation sequences (or other data) compiled from recorded electrograms 21 in representative visual indicia or imagery superimposed on the rendered anatomical map 20, (3) displaying a representation 39, incorporating real-time location and orientation values, of distal end assembly 28 within heart chamber 36, and (4) displaying on display device 27 sites of interest such as places where ablation energy has been applied. One commercial product embodying elements of the system 10 is available as the CARTO™ 3 System, available from Biosense Webster, Inc., 31 Technology Drive, Suite 200, Irvine, CA 92618.

Reference is now made to FIG. 5A, which is a flowchart 300 describing a calibration algorithm performed by processor 22, according to an example of the present disclosure.

The algorithm of flowchart 300 is assumed to be performed by processor 22.

In an initial calibration step 304 of the flowchart, performed prior to the ablation procedure for which distal end assembly 28 is being used, the distal end assembly is calibrated. A calibration process applies known torques to assembly 28, and for each torque applied the average angular deflection, i.e., the torsion, of sensors of assembly 29 is registered, measured relative to distal end 19 of shaft 37. As explained above position sensor 35 on distal end 19 of shaft 37 (to which assembly 28 is attached) measures the orientation of the distal end 19 in 3D.

The deflection of each sensor from its unconstrained location is measured from the sensor signals generated in response to the magnetic fields transmitted from location pad 25 and/or coils 41, as described above. The torques may be applied by any convenient method, such as by twisting the distal end of assembly 26, and monitoring the torque needed for the twist.

In a storage step 306, as a result of the calibration process, processor 22 stores a correspondence between the torque applied to assembly 28 and the average angular deflection of position sensors of assembly 29 and/or the angular deflection of the distal structure 34. The correspondence may be in any convenient form, such as a look-up table or a model-based relation.

In a disclosed example the correspondence is model-based, and assumes that assembly 28 behaves elastically, having a direct proportionality according to equation (1):

$$T = k \cdot \theta \tag{1}$$

where T is the torque applied to the assembly, measured in N·m,

θ is the average angular deflection of sensors of assembly 29, measured in degrees, and k is the constant of proportionality of equation (1), corresponding to the spring constant of the assembly.

In step 306, processor 22 calculates spring constant k of the assembly.

FIG. 5B is a flowchart 310 describing an operational algorithm performed by processor 22 during an ablation procedure, according to an example of the present disclosure. In the procedure, physician 24 inserts catheter 14 into heart 12 until distal assembly 28 is in a desired target location contacting wall 31. Processor 22 uses the algorithm to ascertain a torque on distal end assembly 28, as well as respective forces on electrodes 26 of the assembly as a result of the exerted torque.

The following description of flowchart 310 assumes that the correspondence between torque and average angular deflection given by equation (1) applies, and those having ordinary skill in the art will be able to adapt the description, mutatis mutandis, for other types of correspondence.

In a measurement step 308 processor 22 records the measured positions of sensors of assembly 29. From the measured positions with respect to shaft distal end 19 the processor calculates an average angular deflection of the sensors, i.e., the torsion of distal end assembly 28. It will be understood that sensors of assembly 29 do not necessarily deflect symmetrically with respect to the z-axis. For example, the angular deflection may be asymmetric if distal end assembly 28 deflects as a whole with respect to shaft distal end 19.

The average angular deflection of sensors of assembly 29 is assumed to be $\theta_m$.

Processor 22 uses the calculated value of the average angular deflection, and the spring constant k of the assembly determined in calibration step 304 of flowchart 300, to calculate the overall torque $T_m$ on the assembly, according to equation (2):

$$T_m = k \cdot \theta_m \qquad (2)$$

The torque on assembly 28 is produced by electrodes 26 contacting wall 31, and in an enumeration step 312 processor 22 determines the number of electrodes contacting the wall. The processor may identify which electrodes of electrodes 26 contact tissue of wall 31 using impedance-based measurements, as described above.

For each electrode 26 identified as contacting wall 31, processor 22 also records the location of the electrode. The location may be calculated based on the measured torsion of the electrode, or alternatively or additionally using impedance-based measurements as: for example is described in reference to FIG. 1. Further alternatively or additionally, the location may be recorded using the known locations of the electrodes on splines 13, and the dimensions of the splines.

From the recorded location for each electrode processor 22 calculates a vector, comprising a distance and a direction, from the electrode to the axis of assembly 28, i.e., the z-axis.

It will be understood that each electrode contacting tissue of wall 31 contributes to the overall torque on assembly 28, so that the calculated vector corresponds to the lever arm vector of the torque generated by the electrode.

In an electrode-force step 316, processor 22 uses the results calculated in steps 308 and 312 to estimate the torsional force on each electrode.

In a disclosed example, the measured overall torque $T_m$ is assumed to be evenly distributed amongst all the contacting electrodes. In this case, the magnitude of the torsional force on each electrode is given by equation (3):

$$F_E = \frac{T_m}{n \cdot d_E} \qquad (3)$$

where $F_E$ is the torsional force on an electrode E of electrodes 26, $T_m$ is the overall torque on assembly 28, calculated in equation (2), n is the number of electrodes 26 in contact with tissue of wall 31, determined in step 312, and $d_E$ is the distance of electrode E from the axis of assembly 28, also determined in step 312.

Equation (3) gives the magnitude of the torsional force on electrode E. The direction of the torsional force on electrode E is orthogonal to the axis of symmetry of assembly 28, and is also orthogonal to the lever arm vector of electrode E.

The results described above, i.e., the values generated from equations (2) and (3), as well as the directions of the forces on the electrodes of the distal end assembly, may be provided to physician 24, for example using display device 27. For a given electrode the results may be combined with the force resulting from the electrode pressing against the tissue in a non-torsional manner, and the overall resulting force on the given electrode may be provided to physician 24.

EXAMPLES

Example 1. Apparatus for measuring a torque, comprising:

a probe (14), comprising:

a shaft (37) having a shaft distal end (19);

a distal end assembly (28), configured to be inserted into an organ of a human subject, having a distal termination (34) and a proximal termination (16) connected to the shaft distal end; and a position sensor assembly (29), attached to the distal end assembly in proximity to the distal termination thereof, the position sensor assembly being configured to provide signals indicative of a three-dimensional (3D) position and orientation of the distal termination with respect to the shaft distal end; and a processor (22), configured to compute a torsion of the distal termination with respect to the proximal termination in response to the signals from the position sensor assembly, and compute the torque on the distal end assembly in response to the torsion and a predetermined correspondence between the torsion and the torque.

Example 2. The apparatus according to example 1, and comprising a shaft position sensor (35), attached to the shaft distal end, configured to provide a signal indicative of an orientation of the shaft, and wherein the processor is configured to compute the torsion in relation to the orientation of the shaft.

Example 3. The apparatus according to example 1, and comprising a magnetic field generator (41) attached to the shaft distal end, and wherein the signals from the position sensor assembly are generated in response to a magnetic field from the generator, and wherein the processor is configured to compute the torsion in relation to the orientation of the shaft.

Example 4. The apparatus according to example 1, wherein the predetermined correspondence is based on modeling the distal end assembly as an elastic assembly.

Example 5. The apparatus according to example 1, and comprising a plurality of electrodes (26) attached to the distal end assembly, wherein the processor is configured to identify electrodes contacting tissue of the organ, and to evaluate a number of the contacting electrodes, and compute an electrode-torque on a given electrode of the contacting electrodes in response to the number and the torque.

Example 6. The apparatus according to example 5, wherein the processor is configured to determine a distance of the given electrode to a torsion axis connecting the proximal termination to the distal termination, and compute a magnitude of a force on the given electrode in response to the electrode-torque and the distance.

Example 7. The apparatus according to example 5, wherein the processor is configured to determine a vector from the given electrode to a torsion axis connecting the proximal termination to the distal termination, and compute a direction of a force on the given electrode in response to the vector and an orientation of the torsion axis.

Example 8. The apparatus according to example 5, wherein the processor is configured to determine a force on the given electrode in response to the given electrode pressing on the tissue in a non-torsional manner.

Example 9. The apparatus according to example 1, wherein the distal end assembly comprises a balloon.

Example 10. The apparatus according to example 1, wherein the distal end assembly comprises a plurality of splines.

Example 11. A method for measuring a torque, comprising:

providing a probe (14), comprising:
  a shaft (37) having a shaft distal end (19);
  a distal end assembly (28), configured to be inserted into an organ of a human subject, having a distal termination (34) and a proximal termination (16) connected to the shaft distal end; and
  a position sensor assembly (29), attached to the distal end assembly in proximity to the distal termination thereof, the position sensor assembly being configured to provide signals indicative of a three-dimensional (3D) position and orientation of the distal termination with respect to the shaft distal end;
  computing a torsion of the distal termination with respect to the proximal termination in response to the signals from the position sensor assembly; and
  computing the torque on the distal end assembly in response to the torsion and a predetermined correspondence between the torsion and the torque.

Example 12. The method according to example 11, and comprising attaching a shaft position sensor (35), configured to provide a signal indicative of an orientation of the shaft, and computing the torsion in relation to the orientation of the shaft.

Example 13. The method according to example 11, and comprising attaching a magnetic field generator (41) to the shaft distal end, wherein the signals from the position sensor assembly are generated in response to a magnetic field from the generator, and computing the torsion in relation to the orientation of the shaft.

Example 14. The method according to example 11, wherein the predetermined correspondence is based on modeling the distal end assembly as an elastic assembly.

Example 15. The method according to example 11, and comprising attaching a plurality of electrodes (26) attached to the distal end assembly, identifying electrodes contacting tissue of the organ, evaluating a number of the contacting electrodes, and computing an electrode-torque on a given electrode of the contacting electrodes in response to the number and the torque.

Example 16. The method according to example 15, and comprising determining a distance of the given electrode to a torsion axis connecting the proximal termination to the distal termination, and computing a magnitude of a force on the given electrode in response to the electrode-torque and the distance.

Example 17. The method according to example 15, and comprising determining a vector from the given electrode to a torsion axis connecting the proximal termination to the distal termination, and computing a direction of a force on the given electrode in response to the vector and an orientation of the torsion axis.

Example 18. The method according to example 15, and comprising determining a force on the given electrode in response to the given electrode pressing on the tissue in a non-torsional manner.

Example 19. The method according to example 11, wherein the distal end assembly comprises a balloon.

Example 20. The method according to example 11, wherein the distal end assembly comprises a plurality of splines.

The examples described above are cited by way of example, and the present disclosure is not limited by what has been particularly shown and described hereinabove. Rather the scope of the disclosure includes both combinations and sub-combinations of the various features described hereinabove, as well as variations and modifications thereof which would occur to persons skilled in the art upon reading the foregoing description and which are not disclosed in the prior art.

The invention claimed is:

1. Apparatus for measuring a torque, comprising:
  a probe, comprising:
    a shaft having a shaft distal end,
    a distal end assembly, configured to be inserted into an organ of a human subject, the distal end assembly having:
      a distal termination,
      a proximal termination connected to the shaft distal end, and
      a longitudinal axis extending from the proximal termination to the distal termination, and
    a position sensor assembly, attached to the distal end assembly in proximity to the distal termination thereof, the position sensor assembly being configured to provide signals indicative of a three-dimensional (3D) position and orientation of the distal termination with respect to the shaft distal end; and
  a processor, configured to:
    compute a torsion of the distal termination with respect to the proximal termination, about the longitudinal axis, in response to the signals from the position sensor assembly, and
    compute the torque on the distal end assembly, about the longitudinal axis, in response to the torsion and a predetermined correspondence between the torsion and the torque on the distal end assembly.

2. The apparatus according to claim 1, further comprising a shaft position sensor, attached to the shaft distal end, configured to provide a signal indicative of an orientation of the shaft, the processor being configured to compute the torsion in relation to the orientation of the shaft.

3. The apparatus according to claim 1, further comprising a magnetic field generator attached to the shaft distal end, and the signals from the position sensor assembly being generated in response to a magnetic field from the generator, and the processor being configured to compute the torsion in relation to the orientation of the shaft.

4. The apparatus according to claim 1, the predetermined correspondence being based on modeling the distal end assembly as an elastic assembly.

5. The apparatus according to claim 1, further comprising a plurality of electrodes attached to the distal end assembly, the processor being further configured to:

identify electrodes contacting tissue of the organ, evaluate a number of the contacting electrodes, and compute a torque on a given electrode of the contacting electrodes in response to the number and the torque on the distal end assembly.

6. The apparatus according to claim 5, the processor being further configured to:

determine a distance of the given electrode to the longitudinal axis, and compute a magnitude of a force on the given electrode in response to the torque on the given electrode and the distance.

7. The apparatus according to claim 5, the processor being further configured to:

determine a vector from the given electrode to the longitudinal axis, and compute a direction of a force on the given electrode in response to the vector and an orientation of the longitudinal axis.

8. The apparatus according to claim 5, the processor being configured to determine a force on the given electrode in response to the given electrode pressing on the tissue in a non-torsional manner.

9. The apparatus according to claim 1, the distal end assembly comprising a balloon.

10. The apparatus according to claim 1, the distal end assembly comprising a plurality of splines.

11. A method for measuring a torque, comprising:

providing a probe, comprising:

a shaft having a shaft distal end, a distal end assembly, configured to be inserted into an organ of a human subject, the distal end assembly having:

a distal termination, a proximal termination connected to the shaft distal end, and a longitudinal axis extending from the proximal termination to the distal termination, and a position sensor assembly, attached to the distal end assembly in proximity to the distal termination thereof, the position sensor assembly being configured to provide signals indicative of a three-dimensional (3D) position and orientation of the distal termination with respect to the shaft distal end;

computing a torsion of the distal termination with respect to the proximal termination, about the longitudinal axis, in response to the signals from the position sensor assembly; and computing the torque on the distal end assembly, about the longitudinal axis, in response to the torsion and a predetermined correspondence between the torsion and the torque on the distal end assembly.

12. The method according to claim 11, the shaft further including a shaft position sensor, the shaft position sensor being configured to provide a signal indicative of an orientation of the shaft, the method further comprising computing the torsion in relation to the orientation of the shaft.

13. The method according to claim 11, the shaft further including a distal end with a magnetic field generator, the signals from the position sensor assembly being generated in response to a magnetic field from the magnetic field generator, the method further comprising computing the torsion in relation to the orientation of the shaft.

14. The method according to claim 11, the predetermined correspondence being based on modeling the distal end assembly as an elastic assembly.

15. The method according to claim 11, the distal end assembly further including a plurality of electrodes, the method further comprising:

identifying electrodes contacting tissue of the organ, evaluating a number of the contacting electrodes, and computing a torque on a given electrode of the contacting electrodes in response to the number and the torque on the distal end assembly.

16. The method according to claim 15, further comprising:

determining a distance of the given electrode to the longitudinal axis, and computing a magnitude of a force on the given electrode in response to the torque on the given electrode and the distance.

17. The method according to claim 15, further comprising:

determining a vector from the given electrode to the longitudinal axis, and computing a direction of a force on the given electrode in response to the vector and an orientation of the longitudinal axis.

18. The method according to claim 15, further comprising determining a force on the given electrode in response to the given electrode pressing on the tissue in a non-torsional manner.

19. The method according to claim 11, the distal end assembly comprising a balloon.

20. The method according to claim 11, the distal end assembly comprising a plurality of splines.

\* \* \* \* \*